US007400392B2

(12) United States Patent
Tillmann

(10) Patent No.: US 7,400,392 B2
(45) Date of Patent: Jul. 15, 2008

(54) APPARATUS FOR HANDLING OF A DISKLIKE MEMBER, ESPECIALLY FOR HANDLING OF A WAFER

(75) Inventor: Ralf Tillmann, Mannheim (DE)

(73) Assignee: Integrated Dynamics Engineering GmbH, Raunheim (DE)

( * ) Notice: Subject to any disclaimer, the term of this patent is extended or adjusted under 35 U.S.C. 154(b) by 138 days.

(21) Appl. No.: 11/093,472

(22) Filed: Mar. 30, 2005

(65) Prior Publication Data

US 2005/0237520 A1    Oct. 27, 2005

(30) Foreign Application Priority Data

Apr. 7, 2004    (DE) .................. 10 2004 017 114

(51) Int. Cl.
*G01N 21/00* (2006.01)
(52) U.S. Cl. .................................. 356/237.4
(58) Field of Classification Search ............. 356/237.4, 356/124, 399–402; 901/28, 30, 46
See application file for complete search history.

(56) References Cited

U.S. PATENT DOCUMENTS 4,783,107 A  *  11/1988  Parker et al. .............. 294/88
5,105,147 A  *   4/1992  Karasikov et al. ......... 324/537
6,242,879 B1 *   6/2001  Sagues et al. .............. 318/567
6,678,581 B2 *   1/2004  Hung et al. ................ 700/245
2004/0012363 A1  1/2004  Simondet ............... 318/568.21

FOREIGN PATENT DOCUMENTS

| JP | 2000-162133 | 6/2000 |
| WO | WO 02/02282 A1 | 1/2002 |
| WO | WO 03/027652 A1 | 4/2003 |

* cited by examiner

*Primary Examiner*—Tarifur R. Chowdhury
*Assistant Examiner*—Isiaka O Akanbi
(74) *Attorney, Agent, or Firm*—Ohlandt, Greeley, Ruggiero & Perle, L.L.P.

(57) ABSTRACT

There is provided an apparatus for handling a disklike member having a surface, especially for handling of a wafer, including a robot for carrying out at least an angular motion in a defined moving plane, an end-effector for holding the disklike member, and a wrist member operatively interconnecting said robot with said end-effector. The wrist member provides at least a motion of the end-effector about an axis in a plane of the surface of the disklike member. An inclining motion of said disklike member is achieved by combining the angular motion of the robot and the motion about the axis in the plane of the surface.

12 Claims, 5 Drawing Sheets

APPARATUS FOR HANDLING OF A DISKLIKE MEMBER, ESPECIALLY FOR HANDLING OF A WAFER

CROSS-REFERENCE TO RELATED APPLICATION

The present application is claiming priority of German Patent Application No. 10 2004 017 114.9, filed on Apr. 7, 2004, the content of which is herein incorporated by reference.

BACKGROUND OF THE INVENTION

1. Field of the Invention

The invention relates to an apparatus for handling of a disklike member, and an apparatus for optically inspecting a surface of a disklike member, and an end-effector means for holding a disklike member.

2. Description of Related Art

Apparatus for handling of a disklike member and for optically inspecting a surface of a disklike member, especially of wafer surfaces, are well known in the art.

Semiconductor wafers are produced by complicated multi-step processes in a clean room environment. The production of sophisticated electronic chips from wafers may include as many as about 150 steps. Technologies in the submicron range are very delicate, and there always exists a chance of error or malfunction at each of the many stages, which ought to be discerned as soon as possible. Inspection during the production process and at its end is an imperative stage of the production process and there exists a real need for effective inspection means, capable of inspecting a large number of wafers in an accurate manner within a reasonable time period.

To this end, in world-wide Semiconductor Fabrications, optical measurement tools are used for inspecting and analysing of defects on the wafer surface, which follows an optical characterisation and/or classification of the defects.

This analysis is done on the various measurement spot sizes with a microscope, which is called the Micro-Station, and also on larger areas on the wafer up to the whole wafer surface on the front and on the back side of the wafer. The measurement is carried out in a separate station which is called the Macro-Station. Within the Macro-Station the surface of the wafer is optically inspected by irradiating the surface with light. This kind of measurement is also referred to as Bright-Light-Inspection.

The Bright-Light-Inspection measurement on a wafer is done to check certain properties of the surface which can be made visible by shining light onto a surface of the wafer and looking to the reflected light at a certain angle. The color and the intensity under given angles between the wafer, the light source and an operator (in most cases the naked eye, seldom a camera) is giving the measurement results.

For that purpose, typically, the wafer will by positioned in a bright light beam and the surface of the wafer will be check with the naked eye, while the angle of the wafer surface is changed with respect to the eye and the light source. To be able to get all the required angles the wafer has to be rotated around two orthogonal axis's which are in plane with the wafer surface. FIG. 1 shows the respective co-ordination System of the wafer and the three degrees of rotation together with the rotating axis in-plane.

Today this measurement is done in a special set-up which is holding the wafer. This wafer holding mechanism incorporates the moving parts which are used to change the angle of the wafer surface to the light source. An example of such an holding mechanism is disclosed in JP-A 162133.

The major disadvantage of this kind of system is that it needs a special and quite complicated structural set-up in the Macro-Station which on the one side increases the costs of the Macro-Station and the footprint of it, and which in turn gives rise to higher maintenance costs in a quite expensive clean room environment. Moreover the handling expenditure increases since the handling robot has to place and pick the wafer to or from the holding mechanism. This is even more important if one takes into account that the Macro-station is often used in conjunction with a Micro-station. The additional handling decreases the throughput numbers of the system drastically.

These and other disadvantages have lead to the object of the present invention to provide an apparatus for handling of a disklike member or wafer, which avoids the described disadvantageous with respect to the handling and/or inspection of a wafer, which is simpler in design, has a reduced footprint, and an increase in throughput.

SUMMARY OF THE INVENTION.

The inventive solution for this problem is obtained by an apparatus for handling of a disklike member an apparatus for optically inspecting a surface of a disklike member and an end-effector means.

Further refinements and advantageous developments are part of the respective dependent claims.

Thus far, in general, the invention is an apparatus for handling of a disklike member especially for handling of a wafer, comprising robot means adapted to carry out at least an angular motion in a defined moving plane, and end-effector means for holding the disklike member, wherein said apparatus comprises a wrist member operatively interconnecting said robot means with said end-effect means; wherein said wrist member at least provides a motion of said end-effector about an axis in plane with said surface, thus an inclining motion of said disklike member is achieved, if said angular motion and said motion about said in-plane-axis is combined.

Thus the invention functionally provides, in a highly advantageous manner, an inclining motion of the wafer such that any angle with respect to an outside reference point like a light source is achievable. Upon the inventive operative structure of the provided handling apparatus, it is, for the first time, possible to use a wafer handling robot directly in a station for bright-light-inspection without the need of a transfer of the wafer to or onto a special set-up. In that way, the invention not only reduces a great deal of hardware, which reduces the footprint needed, it also maximizes the handling speed for a minimum single wafer cycling time preferably in a semi-automatic or automatic defect inspection process.

According to a further development of the invention the robot means and the end-effector are adapted to provide that the surface of the disklike member lies parallel inside the moving plane, and that its symmetry axis lies parallel, but, in the first place does not concur with said second axis. This gives the possibility of a precise positioning of the disklike member or wafer in the handling process, and/or with respect to an outside light source during bright light inspection. Moreover, it is provided that the center of the disklike member or wafer is moved on a circular ring about the second axis. The latter is also referred to as Theta-motion.

Further, it is provided that the robot means and/or the wrist member and/or the end-effector is adapted to carry out a rotating movement of said disklike member about an axis perpendicular to said surface including said center.

Thus far, in a highly advantageous further development the inventive apparatus uses an end-effector with an edge-gripping mechanism according to WO 02/02282 A1 which is hereby incorporated by reference. This end-effector, for instance, gives the possibility to rotate the disklike member about its symmetry axis. This, however, enables the inventive apparatus during the inclining motion, to correct the rotation of the robot at the disklike member or wafer level, whereby not only the angle of the surface can be adjusted, but also the orientation of the wafer (rotation angle of the wafer) can be kept constant.

Moreover, advantageously, for the inventive apparatus well known and easily available so called three axis robots with at least one robot arm can be applied. These robots comprise three axis of motion. There is a R-axis-motion, defining the y-axis, which corresponds to a radially directed linear horizontal movement, a Z-axis-motion, which is a vertical linear movement , and a Theta-direction-motion which is a motion around the Z-axis. Generally, the Z-axis is identical with the symmetry axis of the body of the robot. In this case, both the R-axis and the Theta-axis-motion are needed to horizontally position the end-effector and the wafer, respectively, i.e. for providing the angular motion of the robot means in a plane. Yet, for bright-light-inspection according to the present invention the Theta-motion about the Z-axis of the robot corresponding to the second axis as referred to above is used for the combined motion according to the invention.

With reference to another further development of the present invention the wrist member comprises a rotating or rolling mechanism which provides the rotating or rolling movability of the end-effector, attached to it or to its robot arm, about the first axis, which can but need not correspond to the R-axis. However, according to the invention the combination of the Theta- and the rolling-axis-motion can be used for generating an inclining motion of the end-effector or disklike member or wafer to produce any angle with respect to the rolling-rotated wafer surface and the light source of a bright-light-inspection station.

For that purpose the rotating mechanism favorably further comprises a driving mechanism with a driving motor, which drives at least one driving wheel. Additionally to the driving wheel, according to a further development, a support wheel is provided that is, preferably, in horizontal alignment with the driving wheel for balancing the driving mechanism, wherein the driving wheel and the support wheel hold the end-effector.

Moreover, appropriately, the inventive apparatus also comprises control means for controlling the motions about the axis.

Beside the above described handling apparatus, the invention refers also to an apparatus for optically inspecting a surface of a disklike member, especially for optically inspecting of a wafer surface, comprising at least a first inspection region including an apparatus as lined out above, and an illumination device.

The inspection apparatus further comprises a second inspection region including a micro-station or microscope for inspecting the object surface. Advantageously, the second inspection region is and can be modularly coupled with the first inspection region. Thus, it is possible to include into the inventive inspection apparatus a variety of different types of microscopes depending on the individual needs.

Moreover, control means or units are part of the inventive apparatus for controlling the movements of the robot means, especially the motion between the different modular elements. Further more the claimed apparatus comprises a construction frame for to accommodate the different modules or the Macro- and Micro-Station.

Another possible further development of the inventive inspection apparatus includes a passive and/or active vibration isolation system. Preferably the vibration isolation is applied to the second inspection region comprising the microscope.

Yet, it is also an object of the present invention to provide end-effector means comprising holding means for holding a disklike member, particularly a wafer, and a movable wrist member, which allows the end-effector means to move about a rotating axis. This end-effector means comprises a rolling mechanism as described above. Moreover, it is provided that the inventive end-effector means comprises an edge-gripping mechanism according to WO 02/02282 A1.

BRIEF DESCRIPTION OF THE DRAWINGS.

The invention together with additional features and advantageous thereof will be best understood from the following description.

It is shown.

DESCRIPTION OF THE INVENTION.

Figure 1:
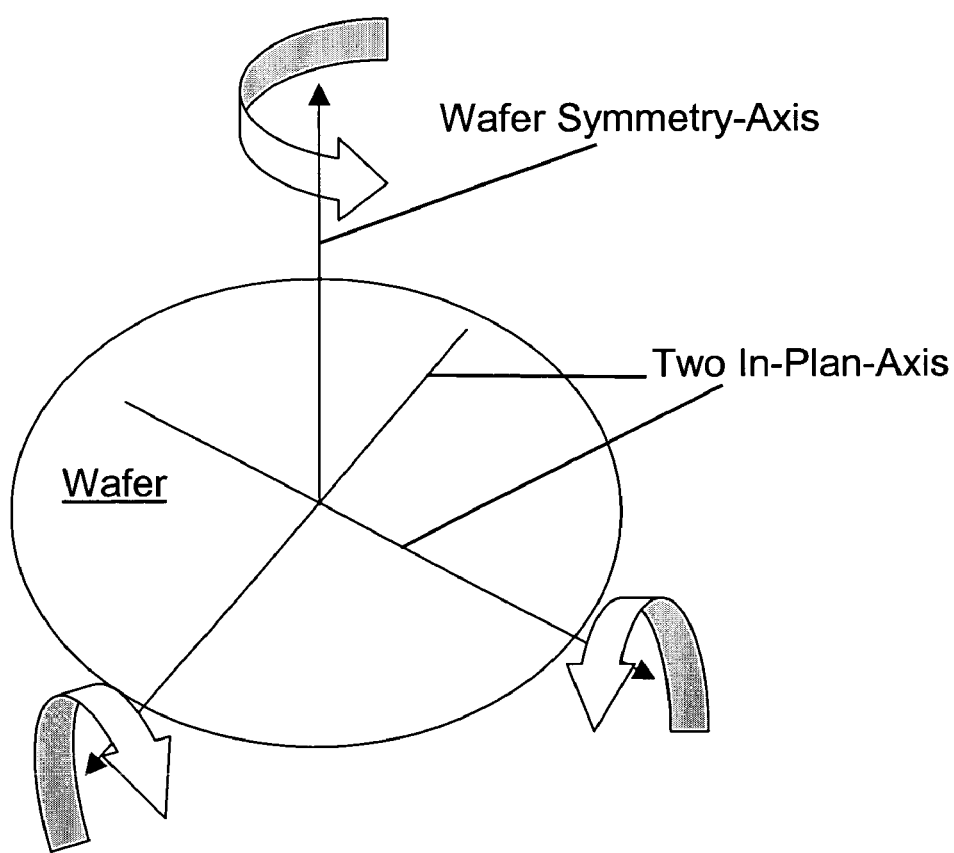
FIG. 1 the coordination system of a wafer and the three degrees of rotation, where two axis are in plane with the wafer surface, FIG. 2 one embodiment of a handling apparatus according to the invention, FIG. 3 the coordination system of an R, Theta, Z-Robot, FIG. 4 a top view of the coordination system of FIG. 3, FIG. 5: an example of an inventive rolling or flipping mechanism.
Figure 2:
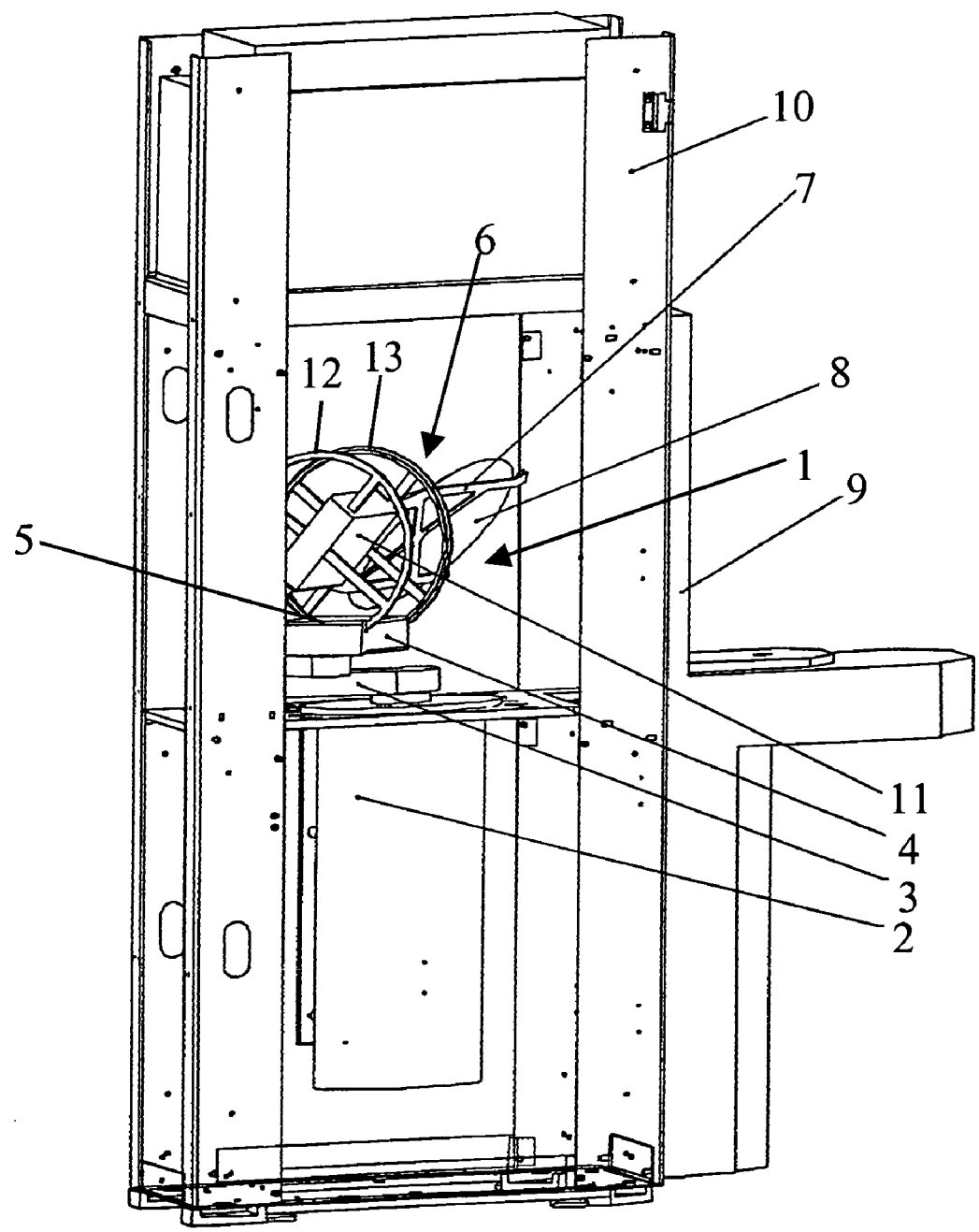

FIG. 2 gives an overview of one embodiment of the inventive apparatus 1. The apparatus comprises four main components, namely a robot body 2, a robot arm 3, a rotating or rolling mechanism 4, 5, providing a rotating or rolling axis, and an end-effector 6. All these components are housed in a frame 10, to which a front opening unified pod 9, generally abbreviated FOUP, might be attached to.

The robot body 2 includes motor drives for driving the robot arm 3 and the end-effector 6, and a robot controller, both not shown in FIG. 2. End-effector 6 is used to grab and hold wafer 8, and robotic arm 3 including various motors and mechanical mechanisms not shown in the Figures, moves end-effector 6 and the wafer that it holds within its grasp 7.

Figure 3:
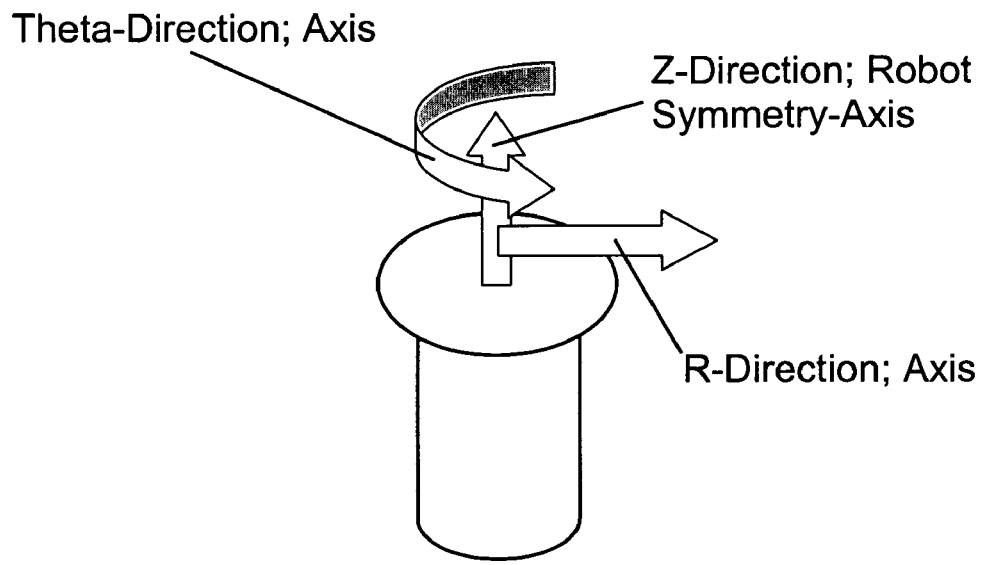
Figure 4:
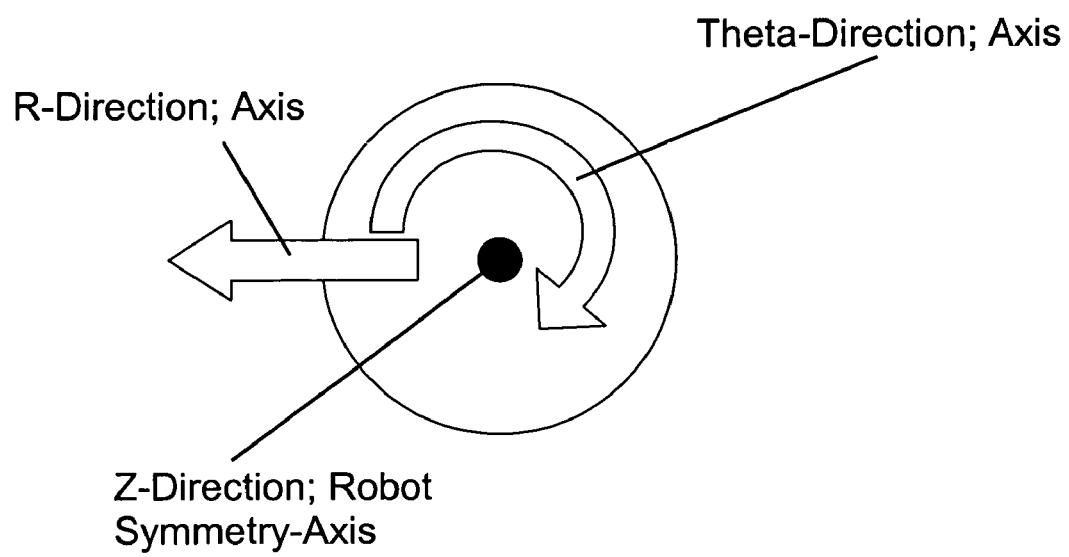

For the handling of single wafer in an Semiconductor Fabric robot 2 typically has three positioning axis's (FIGS. 3 and 4) One axis to move the wafer 8 with its arm vertically up and down, called z-axis, and at least two other axis's to move it horizontally from one station to another in the production process, typically a Theta and an R-axis. These types of robots are well known in the art and are not further described hereinafter in detail.

By using a robot 2 with its positioning axis's (R, Theta, Z) and the rolling capacity of the rotating mechanism 5 about an axis in plane with the wafer surface 8 and perpendicular to the z-axis a combined movement of the wafer 8, grabbed by the end-effector 6, along the Theta axis can be provided. Thus an inclining motion of the wafer 8 is achieved which allows to produce any angle with respect to an outside point like a light source (not shown). For convenience and simplicity the symmetry axis of the wafer 8 can be identical to the rotating axis z of the robot 2 by adjusting the R-postion to the robot 2 accordingly in such a way that the center of the wafer is always on the Theta-axis, even if the wafer is flipped or if rotations accrue by the rolling or the Theta-axis. This means that the center of the wafer 2 is not changed while the angle is changing.

A further improvement can be achieved if an end-effector is used as it is disclosed in the WO 02/02282 A1. To this end the inventive apparatus would, in addition to the rotating functionality, also have the possibility to rotationally orient the wafer 8 in its horizontal plane. Thereby a compensation for the rotation of the wafer 8 introduced by the Theta axis is provided. By combining the motions along or about the three axis, namely the Theta-, the rolling axis, and the symmetry axis of the wafer surface perpendicular to the wafer surface, the angle of the wafer 8 can be adjusted while the orientation of the wafer 8 is kept constant.

As discussed, the rotating or flipping mechanism 5 (FIG. 2) provides a fourth moving axis of the robot 2 and/or a second moving axis to the end-effector 6, which is also referred to as rolling axis. For that purpose a flipper 4 is affixed to the body 11 of end-effector via wheels 12, 13.

Figure 5:
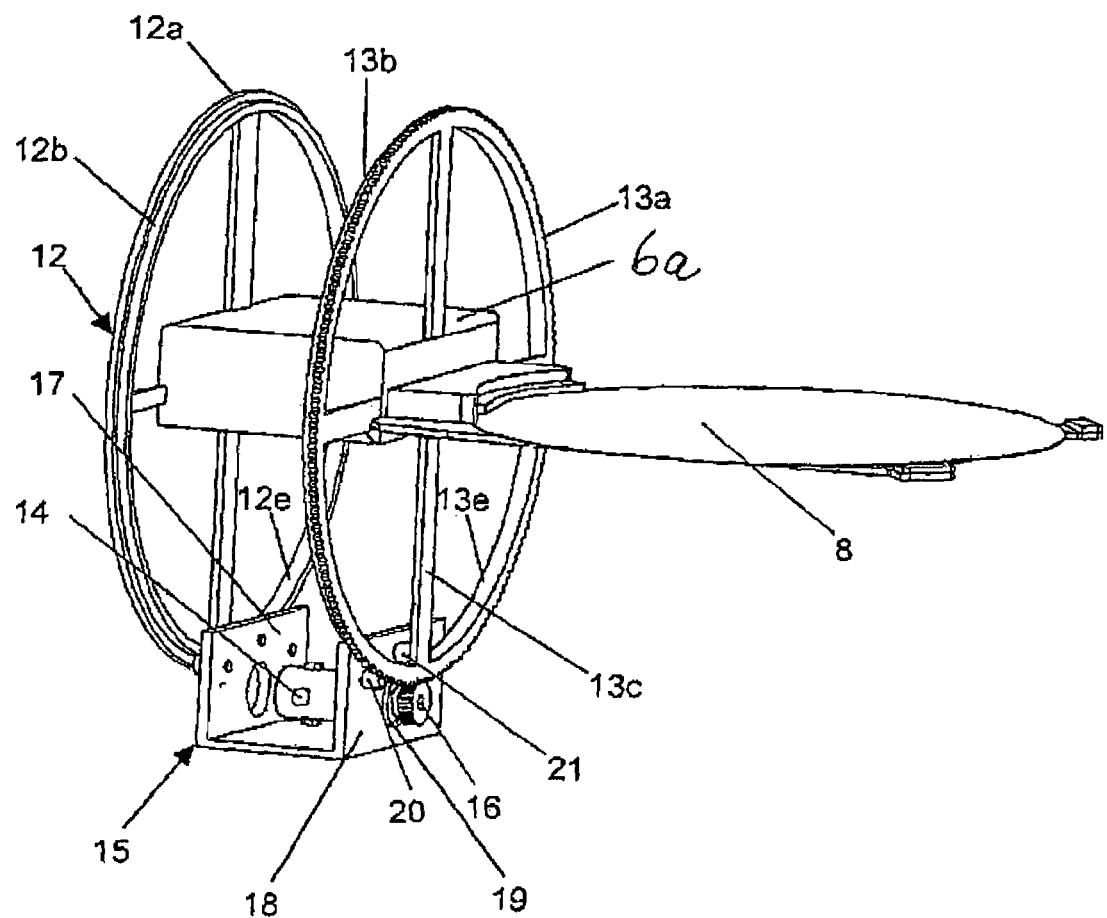

FIG. 5 shows the rotating mechanism 5 in greater detail. Inside the flipper housing 4 (FIG. 2) a bracket 15 with a U-shape is provided which carries the wheels 12, 13. With respect to the wheels, a rear supported wheel 12 and a front driven wheel 13 can be differentiated. The front wheel 13 is a gear wheel which is driven by the driving pinion 16 of a driving motor 14. Each of the wheels has a wheel rim with a step-like or L-shaped profile section, i.e. each of the wheels comprises two neighbouring rims, an inner 12b, 13band an outer rim 12a, 13a, of different rim diameter. For supporting the rim the wheels are equipped with star spokes 12c, 12d, 13c, 13d. The star spokes, however, are only attached at the inside of the outer rim part 12a, 13a of the wheels which has the larger rim diameter, so that a guiding surface 12e, 13e on the inside of the inner rim 12b, 13bwith the smaller rim diameter is provided, such that the inner guiding surface 12e, 13e of the inner rim is not interrupted by the spokes 12c, l2d, 13c, l3d along the whole inner circumference. With respect to the front driven wheel 13, the outer rim 13a forms the gear wheel. In between the rear wheel 12 and the front wheel 13, which are truly aligned to each other, the body of end-effector 6 is attached to the spokes 12c, 12d, 13c and 13dof the respective wheels. This is done in a way that the end-effector 6 can be turned or rotated together with the wheels about an axis. This axis lies in a plane with the wafer surface and intersects the midpoints of the rear the front wheels 12,13. The wheels 12 and 13 are arranged or aligned to one another such that the inner rims 12b and 13b are positioned in opposition to each other.

The main body of the driving motor 14 extends between the rear and the front support 17, 18, i.e. between the upright sides of the U, of the bracket 15 and is mounted in a through-hole 19 of the front support 18 such that the pinion 16, attached at one end of the driving motor 14, goes through the hole 19 to co-operate with the driving wheel 13 on the outside of the bracket-front-support 18. The bracket itself is arranged to the lower part of the wheels 12 and 13. There, a part of the bracket rear support 17 and front support 18 lies between the wheels 12 and 13, whereby this overlap is such that the driving pinion 16 and the front wheel 13 form a gear pair.

This gear pair 13, 16 and the driving motor 14 are part of a driving mechanism which causes the end-effector to rotate about the rotating axis as described above. Additionally, the driving mechanism comprises guiding rollers 20, 21 for guiding the wheels in its rotational movement. Since these rollers and their guiding functionality are the same for each of the wheels 12 and 13, the following description is restricted to the rollers guiding the front wheel 13. Two rollers can be seen in FIG. 5 for this purpose. This is the support roller 20 and the guiding roller 21. They are mounted on the outside of the bracket front support 18. Rollers 20 and 21 are supported by bearings (not shown) on corresponding support pins so that they freely rotate. The rollers 20, 21 are mounted out of line to each other. Thus the support bearing 20 supports the front wheel from its underside, whereas the guiding bearing 21 guides the front wheel by rolling its roller on the guiding surface 13e on the inside of the inner rim 13b.

On the basis of the above described mechanism a wrist member is provided that allows a rotating movement of a wafer grasped by an end-effector. However, if this movement is combined with the move-ability of the robot as described above bright light inspection is possible without a separate set-up which holds the wafer and changes the angles of the wafer surface with respect to the light source.

Figure 6:
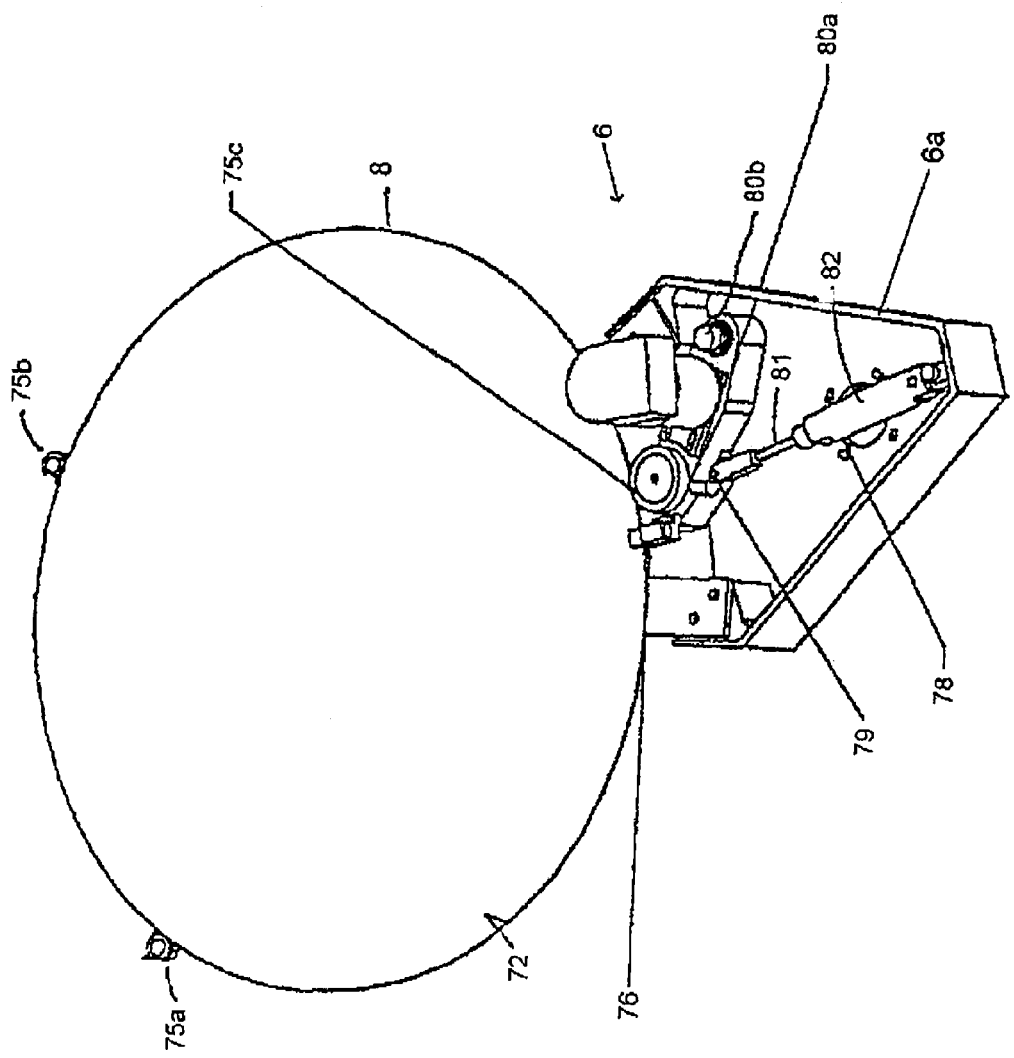
FIG. 6: an end-effector.

Such an end-effector 6 is disclosed in WO 02/02282 A1 and shown in FIG. 6. The end-effector 6 comprises a housing 6a that is mounted between the wheels 12, 13 to which it is attached. The end-effector 6 includes a gripping mechanism and a driving mechanism for rotating the wafer 8 about its vertical axis of symmetry. The gripping and the driving mechanism are combined and comprise a drive roller 75c and idler rollers 75a, 75b. Furthermore, FIG. 6 shows a drive roller housing 80a pivotedly mounted at one end about a pin 80b. A gripper actuator cylinder 78 (e.g., a linear motor or a hydraulically operated device) includes a shaft 81, which moves in and out of a cylinder 82 in response to a control signal. The far end of actuator shaft Bus connected to housing 80a by means of a pin 79. Thus the in and out movement of shaft 81 of actuator 78 causes housing 80a to rotate about pin 80b and, in turn causes drive roller 75c to move, respectively, towards and away from two idler rollers 75a and 75b.

When actuator shaft 81 is retracted into cylinder 82, the separation between drive roller 75c and the idler rollers 75a and 75b becomes large enough to accept wafer 8. Once wafer 8 is located within an area defined by the three rollers 75a, 75b and 75c, actuator shaft 81 is extended out of cylinder 78, thereby pushing drive roller 75c toward the idler rollers until all three rollers contact the outer periphery of and hold wafer 8.

The drive roller 75c can be driven by determined amounts so as to rotate the wafer 8 each time by a predefined angular amount about its axis of symmetry, which is perpendicular to the surface of the wafer 8.

The end-effector 6 further comprises an optical device 78 containing an optical sensing system for optical detecting the presence—or absence—of an alignment feature 72 on the wafer edge as it passes by while the wafer 8 is rotated. In this method, the exact angular location of the alignment feature can be determined as a function of the rotational position of the wafer 8. Thus the angular orientation of the wafer 8 can be precisely incremented.

What is claimed is:

1. An apparatus for handling a disk-like member, comprising:
  a robot for carrying out at least an angular motion in a defined plane of motion;
  a wrist member that can be driven by said robot and forms a rotating mechanism for said disk-like member;
  an end-effector that can be driven by said wrist member, for holding and rotating said disk-like member about an axis perpendicular to a flat surface of said disk-like member, so that a surface of said disk-like member to be inspected can be offered in a desired inclination, wherein said rotating mechanism includes a pair of wheels having an axis of rotation in said flat surface of said disk-like member;

wherein said angular motion of said robot and said rotating motion of said end-effector are combined to achieve said desired inclination of said surface, wherein said end-effector includes a body having an edge-gripping mechanism within that carries the disk-like member, and wherein said body having said edge gripping mechanism is arranged in a space between said pair of wheels and is fixedly connected to said pair of wheels.

2. An apparatus for handling a disk-like member that has a flat surface bounded by a circular edge defining a rotational axis of symmetry perpendicular to said flat surface, comprising:

a frame defining a defined plane of motion, a robot for carrying out angular and linear motions at least in said defined plane of motion relative to said frame, a wrist member in driven connection to said robot to be moved parallel to said defined plane of motion, said wrist member including a driving member and a driven member as well as a guiding and supporting device for guiding and supporting said driven member, said driven member having an axis of rotation that is parallel to said defined plane of motion and, when rotated, causes an inclination of the disk-like member about an axis of inclination, which is parallel to said flat surface of said disk-like member; and an end-effector connected to said driven member of said wrist member, wherein said end-effector includes a gripping mechanism having a device for driving said circular edge of said disk-like member and thus rotating the disk-like member about said rotational axis of symmetry of the disk-like member perpendicular to its flat surface so that said disk-like member can be inclined about any axis of inclination among all axes that are parallel to said flat surface of said disk-like member.

3. The apparatus of claim 2, wherein said frame is designed for housing said handling apparatus in an inner space that has an opening and a rod for inserting into, or removing, the disk-like member from said inner space.

4. The apparatus of claim 2, further comprising:

a pair of wheels arranged parallel to one another and defining a space, wherein said wheels are positioned on said guiding and supporting device; and a body fixedly connected to said pair of wheels, wherein said body is included in said device for rotating the disk-like member, and said body is arranged in said space between said wheels.

5. The apparatus of claim 4, further comprising:

a bracket that carries a driving motor for a driving pinion that engages one wheel of said pair of wheels, wherein said bracket is included on said driving member of said wrist member.

6. The apparatus of claim 4, wherein one of said pair of wheels is a driving wheel.

7. The apparatus of claim 4, wherein one of said pair of wheels is a support wheel.

8. The apparatus of claim 4, wherein said frame encompasses an inner space with an opening and a rod for inserting into, or removing, the disk-like member from said inner space.

9. An apparatus for handling a disk-like member having a flat surface bounded by a circular edge defining a rotational axis of symmetry perpendicular to said flat surface, comprising:

a frame for housing said handling apparatus, a robot for carrying out angular and linear motions at least in a defined plane of motion relative to said frame, a wrist member in driven connection to said robot to be moved parallel to said defined plane of motion, said wrist member including a driving member and a driven member as well as a guiding and supporting device for guiding and supporting said driven member, said driven member having an axis of rotation that is parallel to said defined plane of motion and, when rotated causes an inclination of the disk-like member about an axis of inclination, which is parallel to said flat surface of said disk-like member;

an end-effector connected to said driven member of said wrist member, wherein said end-effector includes a gripping mechanism for holding the disk-like member, and wherein said end-effector also includes a device for driving said circular edge of said disk-like member and rotating the disk-like member about said rotational axis of symmetry of the disk-like member perpendicular to its flat surface;

a pair of wheels arranged parallel to one another and defining a space, wherein said wheels are positioned on said guiding and supporting device; and a body fixedly connected to said pair of wheels, wherein said body is included in said device for rotating the disk-like member, and said body is arranged in said space between said wheels.

10. The apparatus of claim 9, further comprising:

a bracket that carries a driving motor for a driving pinion that engages one wheel of said pair of wheels, wherein said bracket is included on said driving member of said wrist member.

11. The apparatus of claim 9, wherein one of said pair of wheels is a driving wheel.

12. The apparatus of claim 9, wherein one of said pair of wheels is a support wheel.

* * * * *